United States Patent [19]

Wright et al.

[11] 4,067,995
[45] * Jan. 10, 1978

[54] COMPOUNDS, COMPOSITIONS AND METHODS OF USE

[75] Inventors: John B. Wright; Anthony A. Sinkula, both of Kalamazoo, Mich.

[73] Assignee: The Upjohn Company, Kalamazoo, Mich.

[*] Notice: The portion of the term of this patent subsequent to Dec. 3, 1991, has been disclaimed.

[21] Appl. No.: 635,808

[22] Filed: Nov. 28, 1975

Related U.S. Application Data

[63] Continuation of Ser. No. 477,817, June 10, 1974, abandoned.

[51] Int. Cl.² .................. A61K 31/275; C07C 121/78
[52] U.S. Cl. .................. 424/304; 260/239 A; 260/239 BF; 260/326.13 D; 260/465 D
[58] Field of Search .................. 260/465 D; 424/304

[56] References Cited
U.S. PATENT DOCUMENTS

| | | | |
|---|---|---|---|
| 3,639,249 | 2/1972 | Luethi et al. | 252/300 |
| 3,852,324 | 12/1974 | Wright | 260/465 |
| 3,966,965 | 6/1976 | Sellstedt et al. | 424/309 |
| 3,972,911 | 8/1976 | Wright et al. | 260/465 D |
| 3,993,679 | 11/1972 | Hall et al. | 260/465 D |

*Primary Examiner*—Dolph H. Torrence
*Attorney, Agent, or Firm*—Martin B. Barancik

[57] ABSTRACT

It has now been discovered that novel compounds of FIG. 1

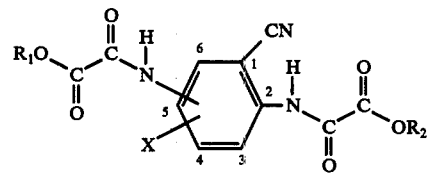

are useful in the prophylactic treatment of sensitized humans and animals for allergy and all anaphylactic reactions of a reagin or non-reagin mediated nature. Additionally, the compounds are intermediates to the diacid or di salts which have utility in the same area as the esters. The compounds are formulated with pharmaceutical carriers for oral, parenteral, inhalation, or rectal means of administration.

15 Claims, No Drawings

COMPOUNDS, COMPOSITIONS AND METHODS OF USE

This is a continuation of application Ser. No. 477,817 filed June 10, 1974, now abandoned.

BRIEF SUMMARY OF THE INVENTION

It has now been discovered that novel compounds of FIG. 1 are useful in the prophylactic treatment of sensitized humans and animals for allergy and all anaphylactic reactions of a reagin or non-reagin mediated nature. Additionally, the compounds are intermediates to the diacid or di salts which have utility in the same area as the esters. The compounds are formulated with pharmaceutical carriers for oral, parenteral, inhalation, or rectal means of administration.

DETAILED DESCRIPTION OF THE INVENTION

In accordance with the invention compounds of FIG. 1, hereinafter referred to as Group I are provided.

$$
\begin{array}{c}
R_1O \\
\diagdown \\
C \\
\diagup \\
O
\end{array}
\begin{array}{c}
O \\
\parallel \\
C \\
\diagup \\
\end{array}
\begin{array}{c}
H \\
| \\
N
\end{array}
\begin{array}{c}
\text{(benzene ring positions 1-6 with substituents)}
\end{array}
\quad (I)
$$

wherein $$-\underset{H}{\overset{|}{N}}-\underset{O}{\overset{\parallel}{C}}-\underset{O}{\overset{\parallel}{C}}-OR_1$$

is at one of the positions 4, 5, and 6 with the proviso that where $$-\underset{H}{\overset{|}{N}}-\underset{O}{\overset{\parallel}{C}}-\underset{O}{\overset{\parallel}{C}}-OR_1$$

is at 4, then when X is at the 3 position, X is selected from the group consisting of hydrogen and alkyl from one to three carbon atoms, inclusive;
  when X is at the 5 position, X is selected from the group consisting of hydrogen, halogen, alkoxy from one to three carbon atoms, inclusive, and cyano; and
  when X is at the 6 position, X is selected from the group consisting of hydrogen and halogen;
5, then when X is at the 3 or 6 position, X is hydrogen, and
  X is at the 4 position, X is selected from the group consisting of hydrogen, halogen, alkyl from one to three carbon atoms, inclusive; and alkoxy from one to three carbon atoms, inclusive;
6, when X is at the 3 or 5 position, X is selected from the group consisting of hydrogen and alkyl from one to three carbon atoms, inclusive; and
  X is at the 4 position, X is selected from the group consisting of hydrogen, alkyl from one to three carbon atoms, inclusive, and cyano;
and $R_1$ and $R_2$ are the same or different and are selected from the group consisting of hydrogen; a physiologically acceptable metal or amine cation; alkyl of one to 12 carbon atoms, inclusive; cycloalkyl of four to eight carbon atoms, inclusive;

$$-(CH_2)_m-\text{phenyl-}Q$$

where $m$ is an integer of 0 to 4, inclusive, and Q is selected from the group consisting of hydrogen, alkyl of one to six carbon atoms, inclusive, phenyl, halogen, trifluoromethyl, hydroxy, alkoxy of one to four carbon atoms, inclusive, amino, nitro, carboxy, cyano, and $$\diagdown N \diagdown \begin{array}{c} R_3 \\ R_4 \end{array}$$

wherein $R_3$ and $R_4$ are the same or different and are selected from the group consisting of hydrogen and alkyl of one to four carbon atoms, inclusive; and $$-(CH_2)_n N \diagdown \begin{array}{c} R_5 \\ R_6 \end{array}$$

wherein $n$ is an integer of 2 to 4, inclusive, and $R_5$ and $R_6$ are the same or different and are selected from the group consisting of hydrogen and alkyl of one to four carbon atoms, inclusive, and when $R_5$ and $R_6$ are taken together with the nitrogen atoms to which they are attached form a saturated heterocyclic of three to six ring carbon atoms, inclusive; with the further proviso that when one of $R_1$ and $R_2$ is hydrogen or a physiologically acceptable metal or amine cation, the other variable is not hydrogen or a physiologically acceptable metal or amine cation.

A further aspect of this invention is compounds of Group I, hereinafter referred to as Group II, where the position of $$-\underset{H}{\overset{|}{N}}-\underset{O}{\overset{\parallel}{C}}-\underset{O}{\overset{\parallel}{C}}-OR_1$$

and the X substituent are as defined in Group I and $R_1$ and $R_2$ are the same or different and are selected from the group consisting of alkyl of one to eight carbon atoms, inclusive;

$$-(CH_2)_m-\text{phenyl-}Q$$

wherein $m$ is an integer of 0 to 4, inclusive, and Q is selected from the group consisting of hydrogen, alkyl of one to four carbon atoms, inclusive, alkoxy of one to four carbon atoms, inclusive, halogen, carboxy and cyano; and cycloalkyl of four to seven carbon atoms, inclusive.

A still further aspect of the invention are compounds of Group I, hereinafter referred to as Group III, wherein

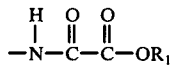

and the substituent X are as in Group I and $R_1$ and $R_2$ are the same or different and are selected from the group consisting of alkyl of four to six carbon atoms, inclusive;

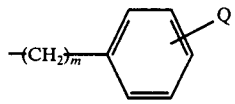

wherein m is 1 or 2 and Q is selected from the group consisting of hydrogen or the ortho or meta isomers of alkyl of one to four carbon atoms, inclusive, alkoxy of one to four carbon atoms, inclusive, fluoro, bromo, chloro, cyano, and carboxy.

Preferred groups of $R_1$ and $R_2$ are Groups I, II, and III above, where $R_1$ is the same as $R_2$. It should be noted that when $R_1$ and $R_2$ of Group I are the same, neither $R_1$ nor $R_2$ can be hydrogen or a physiologically acceptable metal or amine cation.

More preferred are the compounds of the preferred groups above where

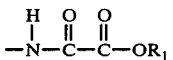

is at the four or five position and X is hydrogen.

As employed in the above disclosure and throughout the specification, the term "halogen" includes fluoro, chloro, bromo, and iodo. The phrase "alkyl of one to 12 carbon atoms, inclusive" includes methyl, ethyl, propyl, butyl, pentyl, hexyl, heptyl, octyl, nonyl, decyl, undecyl, dodecyl, and isomers thereof. Illustrative examples of the isomers are isopropyl, tert. butyl, neopentyl, 2,3-dimethylbutyl, isoheptyl, 2,2,4-trimethyloctyl, 3-propyl-4-methylpentyl, isodecyl, isoundecyl, and isododecyl. When alkyl is limited to a lesser number of carbon atoms, the scoping is intended within that number of carbon atoms. The phrase "a physiologically acceptable metal or amine cation" is that metal or amine which is accepted in a non-toxic manner by a mammal. Illustrative examples of such metals are the alkali metals, e.g., lithium, sodium, and potassium, and the alkaline earth metals, e.g., mgnesium and calcium. Other metals, e.g., aluminum, zinc, and iron are also within the scope of this invention. Illustrative of the amines are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms as well as heterocyclic amines, e.g., piperidine, morpholine, pyrrolidine, piperazine, and lower-alkyl derivatives thereof, e.g, 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltriemethylammonium, phenyltriethylammonium and the like.

The compounds of the invention can be prepared by methods known to the art. For example, methods outlined in U.S. Pat. No. 3,639,249, column 3, line 38, to column 5, line 18, can be used with facility. Diamino substituted benzonitriles with X in appropriate position are suitable starting materials. These compounds are reacted with an $R_1$, with the proviso that $R_1$ is not hydrogen or a physiologically acceptable metal or amine cation, substituted oxalylhalide, preferably the chloride in a suitable solvent and base to form a dioxamate of FIG. 1. This ester can then be transesterified with known reagents and conditions to form a different ester. If less than stoichiometric quantities are employed in the transesterification, esters where $R_1$ and $R_2$ differ are readily prepared. After formation of the ester, less than stoichiometric quantities of reagents can be employed to prepare the half acid and the half metal or amine salt, the other half of the molecule being the ester moiety.

Examples of known starting material precursors include 2,6-dinitro-4-methylbenzonitrile; 5-chloro-2,4-dinitrobenzonitrile; 2-chloro-4,6-dinitrobenzonitrile; and 2,4-dinitro-m-toluinitrile, which can be readily reduced to the corresponding diamino compound. Other starting materials are conveniently prepared by known methods. For example, appropriately X-substituted dinitro benzoic acids can be converted to the analogous cyano compound and then reduced to analogous diamino compounds. The conversion of the acid to the nitrile is readily accomplished by step-wise treatment of the acid with thionyl chloride, ammonia, and phosphorous pentoxide. The reduction of nitro to amino is easily effected by catalytic means such as Raney Nickel, palladium on charcoal or platinum in the presence of hydrogen. Additionally, conventional chemical means are also available for reduction of a nitro grouping to an amine grouping, for example, stannous chloride in concentrated hydrochloric acid and iron in acetic acid and ethanol.

Examples of suitable starting material precursors and/or the method of preparing them are the following: m-alkylbenzoic acid is nitrated with nitric acid to make 2,6-dinitro-3-alkylbenzoic acid and 2,4-dinitro-3-alkylbenzoic acid which are readily separated by chromatography. The carboxy group is converted to cyano by methods previously disclosed above and the nitro groups reduced to amino by one of the aforementioned methods to make 2,6-diamino-3-alkylbenzonitrile and 2,4-diamino-3-alkylbenzonitrile. Alternatively m-halo, preferably fluoro or chloro, benzoic acid can be nitrated to form 2,4-dinitro-5-halo-benzoic acid. This compound can either be reduced to the corresponding diaminobenzonitrile or substituted at the 5-position with alkoxy by subjecting the 2,4-dinitro-5-halobenzoic acid to alkanol attack in a strong base such as KOH. The product of such treatment is 2,4-dinitro-5-alkoxybenzoic acid which is then reduced to the 2,4-diamino-5-alkoxybenzonitrile.

2,5-diamino-4-substituted benzonitriles are prepared in the following manner. Where the substitution is alkyl, the 2-nitro-4-alkylbenzoic acid is converted to the corresponding benzonitrile and then reduced to the corresponding aminobenzonitrile. The resulting 2-amino-4-alkylbenzonitrile is then nitrated with nitric acid to the 2-amino-4-alkyl-5-nitrobenzonitrile which is separated from its isomer by chromatography and reduced to the 2,5-diamino-4-alkylbenzonitrile. In a similar manner, 2,5-diamino-4-halobenzonitrile and the 2,5-diamino-4-alkoxybenzonitrile compounds are prepared from 2-nitro-4-halobenzoic acid and 2-nitro-4alkoxybenzoic acid precursors respectively.

Once the diamino substituted benzonitrile with X in the appropriate position is prepared, it is reacted with an $R_1$ oxalylhalide, for example, n-butyloxalylhalide to form the dioxamate. This reaction is carried out in base and solvent at standard conditions, as exemplified by the art. Examples of suitable solvents are dimethylformamide, dioxane, and tetrahydrofuran. Appropriate bases include triethylamine, N-methylmorpholine, dimethylpiperazine, and N-methylpiperidine.

As stated previously, esters with different $R_1$ and $R_2$ groups are prepared by transesterification. From thereon, half esters are conveniently prepared by standard methods.

Following is an illustrative list of compounds of the invention which can be prepared by the above procedure.

TABLE 1

| X and Ring Position | Ring Position of $-\overset{H}{N}-\overset{O}{C}-\overset{O}{C}-OC_2H_5$ |
|---|---|
| 3H | 4 |
| 3CH$_3$ | 4 |
| 3C$_3$H$_7$ | 4 |
| 5F | 4 |
| 5Cl | 4 |
| 5OC$_2$H$_5$ | 4 |
| 5Oi-C$_3$H$_7$ | 4 |
| 5CN | 4 |
| 6F | 4 |
| 6 Cl | 4 |
| 3H | 5 |
| 4F | 5 |
| 4H | 5 |
| 4Cd$_3$ | 5 |
| 4C$_3$H$_7$ | 5 |
| 4OCH$_3$ | 5 |
| 4Oi-C$_3$H$_7$ | 5 |
| 3H | 6 |
| 4CN | 6 |
| 3C$_2$H$_5$ | 6 |
| 5C$_3$H$_7$ | 6 |
| 4CH$_3$ | 6 |

TABLE II

Each of the compounds of Table I is converted to a dioxamate of FIG. 1 where $R_1$ and $R_2$ are the same and are illustratively exemplified by the following:

| $R_1 = R_2$ |
|---|
| CH$_3$ |
| C$_3$H$_7$ |
| tC$_4$H$_9$ |
| C$_6$H$_{13}$ |
| C$_7$H$_{15}$ |
| iC$_8$H$_{17}$ |
| 2,4-diethylpentyl |
| idecyl |
| dodecyl |
| cyclobutyl |
| cyclopentyl |
| cyclohexyl |
| cycloheptyl |
| cyclooctyl |
| phenyl |
| benzyl |
| phenethyl |
| α,α-dimethylbenzyl |
| 4-(phenyl)butyl |
| α,α-dimethylphenethyl |
| p-chlorophenyl |
| o-isopropylbenzyl |
| m-pentylphenethyl |
| 3-(p-isohexylphenyl)propyl |
| 4-(o-isopropoxyphenyl)butyl |
| m-methoxyphenethyl |
| p-butoxyphenyl |
| m-phenylbenzyl |
| 3-(o-fluorophenyl)propyl |
| m-bromophenethyl |
| p-(trifluoromethyl)phenyl |
| m-hydroxyphenethyl |
| o-aminobenzyl |
| m-nitrophenyl |
| p-carboxyphenethyl |
| m-cyano-α,α-dimethylbenzyl |
| 4-(o-cyanophenyl)butyl |
| o-(methylamino)phenyl |
| m-(diethylamino)benzyl |
| p-(dibutylamino)phenethyl |
| o-(ethylmethylamino)-α,α-dimethylbenzyl |
| 4-[m-(propylamino)phenyl]butyl |
| 2-aminoethyl |
| 3-(methylamino)propyl |
| 4-(ethylamino)butyl |
| 2-(methylpropylamino)ethyl |
| 1-(butylethylamino)-1-methylethyl |
| 2-(1-azetidinyl)ethyl |
| 3-(1-pyrrolidinyl)propyl |
| 4-(hexahydro-1H-azepin-1-yl)butyl |
| $(CH_2)_nN\begin{smallmatrix}CH_3\\C_2H_5\end{smallmatrix}$ |

TABLE III

The compounds of Table II are conveniently to unsymmetrical esters ($R_1 \neq R_2$) by standard means.

TABLE IV

The compounds of Tables II and III are converted by standard means to half esters where either $R_1$ or $R_2$ is hydrogen or a physiologically acceptable metal or amine cation.

The following examples are compounds in accordance with this invention. The compounds are not intended to limit but merely to exemplify the invention.

EXAMPLE 1

Dimethyl N,N'-(4-cyano-m-phenylene)dioxamate a. 2,4-dinitrobenzonitrile

A mixture of 21.2 grams (0.1 mole) of 2,4-dinitrobenzoic acid and 32.0 grams (0.21 mole) of benzenesulfonamide is stirred and heated in an oil bath at 205°–210° for 1 hour and then at 225° for 1 hour and allowed to cool to room temperature under a nitrogen atmosphere. The residue is shaken with methylene chloride and dilute NaOH solution and the methylene chloride layer separated and washed with water. The solvent is removed by distillation. There is obtained 6.05 grams (31%) of material melting at 88°–92°. Recrystallization from ethanol raises the melting point to 100°–2°. The infrared spectrum shows a weak nitrile band at 2200 cm$^{-1}$.

b. 2,4-Diaminobenzonitrile

To a stirred solution of 45.12 grams (0.2 moles) of stannous chloride dihydrate in 100 ml. of concentrated HCl is added, gradually, 5.44 grams (0.0282 moles) of 2,4-dinitrobenzonitrile. An exothermic reaction takes place with the temperature rising to about 80°. The solution is stirred and allowed to come to room temperature over the course of 2 hours. The mixture is made strongly basic by the addition of a 50% sodium hydroxide solution, with cooling, and extracted with methylene chloride. The $CH_2Cl_2$ extracts are dried over anhydrous $MgSO_4$ and the solvent removed. There is obtained 3.0 grams (80%) of a yellow solid melting at 102°–3°. Infrared (mull): 3500, 3350, (NH), 2200 (CN) cm$^{-1}$.

Analysis Calcd. for: $C_7H_7N_3$: C, 63.14; H, 5.30; N, 31.56. Found: C, 62.98; H, 5.35; N, 31.27.

c. Dimethyl N,N'-(4-cyano-m-phenylene)dioxamate

A mixture of 29.0 grams (0.218 mole) of 2,4-diaminobenzonitrile and 255 grams of dimethyl oxalate is refluxed for 3 hours. The excess dimethyl oxalate is distilled off in vacuo. The residue is boiled with 150 ml. of methanol and filtered. The filtrate is poured into 900 ml. of water and the tan precipitate removed by filtration. There is obtained 53.7 grams (81%) of tan needles melting at 155°–160°. The product is boiled in 1800 ml. of methanol and the insoluble material removed by filtration. The filtrate is poured into 2 liters of water, refrigerated, and the precipitate removed by filtration. There is obtained 23.8 grams of fine yellow needles melting at 160°–163°.

Analysis Calcd. for: $C_{13}H_{11}N_3O_6$: C, 51.15; H, 3.63. Found: C, 51.69; H, 3.69.

The infrared and NMR spectra are in agreement.

EXAMPLE 2

Diethyl N,N'-(2-cyano-p-phenylene)dioxamate a. 2,5-Diaminobenzonitrile

To a solution of 80 grams (0.356 mole) of stannous chloride dihydrate in 200 ml. of concentrated hydrochloric acid is added in portions over the course of about 5 minutes, 16.314 grams (0.1 mole) of 5-nitroanthranilonitrile. Water cooling is used and the internal temperature rises to about 50°. Stirring is continued for 4 hours and the mixture is allowed to stand overnight. The reaction mixture is cooled to 5° in an ice-bath and a cold 50% solution of sodium hydroxide added until the mixture is strongly basic. The mixture is extracted with methylene chloride. The methylene chloride extracts are washed with water and the solvent removed by distillation. There is obtained 11.51 grams (86.5%) of material melting at 85°–87°. Recrystallization from benzene-skellysolve B gives material melting at 86°–7°. The infrared spectrum is in agreement.

b. Diethyl N,N'(2-cyano-p-phenylene)dioxamate

To a solution of 13.4 grams (0.112 mole) of 2,5-diaminobenzonitrile and 22.6 grams of triethylamine in 245 ml. of dimethylformamide, cooled to 5°, is added, dropwise, 30.5 grams of ethyl oxalyl chloride. The temperature is kept below 8°. The mixture is stirred in an ice bath for 2 hours and allowed to stand overnight. The precipitate is removed by filtration and the filtrate poured into 1500 ml. of water. The resulting precipitate is removed by filtration and recrystallized from ethanol. There is obtained 33.1 grams (89%) of cream needles melting at 140°–141°.

Analysis Calcd. for: $C_{15}H_{15}N_3O_6$: C, 54.05; H, 4.54; N, 12.61. Found: C, 54.39; H, 4.62; N, 12.80.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of FIG. 1. The preferred method of administration is by inhalation into the lung by means of an aerosol liquid or powder for insufflation.

For oral administration, either solid or fluid unit dosage forms can be prepared. For preparing solid compositions such as tablets, the compound of FIG. 1 is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dispersing a compound of the FIG. I in water or ethanol and mixing with a volatile propellant and placing in a pressurized container having a metering valve to release a predetermined amount of material.

The liquefied propellant employed is one which has a boiling point below 65° F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.2 to about 200 mg. of compound in a single dose, administered parenterally or by inhalation in the compositions of this invention, are effective for preventing allergy attacks. More specifically, the single dose is from about 1.0 to about 20 mg. of compound. The oral and rectal dose is from about 10 to about 400 mg. in a single dose. More specifically, the single dose is from about 20 to about 100 mg. of compound. The dosage to be administered can be repeated up to four times daily.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 3

A lot of 10,000 tablets, each containing 20 mg. of Dimethyl N,N'-(4-cyano-m-phenylene)dioxamate is prepared from the following types and amounts of ingredients:

Dimethyl N,N'-(4-cyano-m-phenylene)-dioxamate: 200 Gm.
Dicalcium phosphate: 1,000 Gm.
Methylcellulose, U.S.P. (15 cps): 60 Gm.
Talc: 150 Gm.
Corn starch: 200 Gm.
Magnesium stearate: 10 Gm.

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever or asthma attacks at a dose of one tablet every 6 hours.

EXAMPLE 4

One thousand tablets, each containing 30 mg. of Dimethyl N,N'-(4-cyano-m-phenylene)dioxamate are prepared from the following types and amounts of ingredients:

Dimethyl N,N'-(4-cyano-m-phenylene)-dioxamate: 30 Gm.
Microcrystalline cellulose NF: 410 Gm.
Starch: 100 Gm.
Magnesium stearate powder: 3 Gm.

The ingredients are screened and blended together and pressed into tablets.

The tablets are useful to protect against food allergy at a dose of one tablet before meals.

EXAMPLE 5

A sterile preparation suitable for intramuscular injection and containing 2.0 mg. of Dimethyl N,N'-(4-cyano-m-phenylene)dioxamate in each milliliter is prepared from the following ingredients:
Dimethyl N,N'-(4-cyano-m-phenylene)-dioxamate: 2.0 Gm.
Benzyl benzoate: 200 ml.
Methylparaben: 1.5 Gm.
Propylparaben: 0.5 Gm.
Cottonseed oil q.s.: 1,000 ml.

One milliliter of this sterile preparation is injected for prophylactic treatment of allergic rhinitis.

EXAMPLE 6

Six hundred ml. of an aqueous suspension containing 4.0 mg. of the Dimethyl N,N'-(4-cyano-m-phenylene)-dioxamate per ml. is prepared as follows:
Dimethyl N,N'-(4-cyano-m-phenylene)-dioxamate: 2.4 Gm.
Sodium chloride: 5 Gm.
Water for injection q.s.: 600 ml.

The compound of the above formulation and sodium chloride are dispersed in sufficient water to make 600 ml. and sterilized.

The liquid is placed in nebulizers designed to deliver 0.25 ml. per spray.

The liquid is inhaled into the lungs every 4 to 6 hours for prevention of asthmatic attacks.

EXAMPLE 7

A powder mixture consisting of 0.1 gram of Dimethyl N,N'-(4-cyano-m-phenylene)dioxamate and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 8

A powder mixture consisting of 0.1 gram of Diethyl N,N'-(2-cyano-p-phenylene)dioxamate and sufficient lactose to make 5 grams of mixture is micropulverized and placed in an insufflator designed to deliver 50 mg. of powder per dose.

The powder is inhaled into the lungs every 4 to 6 hours for prevention of asthmatic attacks.

The powder is inhaled intranasally every 4 hours for prevention of rhinitis.

EXAMPLE 9

Twelve grams of an aerosol composition are prepared from the following ingredients:
Dimethyl N,N'-(4-cyano-m-phenylene)-dioxamate: 0.500 Gm.
Freon 12: 1.440 Gm.
Freon 114: 2,160 Gm.
Water: 7.300 Gm.
Sorbitan monoleate: 0.600 Gm.

The compound is dispersed in the water and chilled to $-30°$ C. and added to the chilled Freons. The 12 grams of compositions are added to a 13 ml. plastic coated bottle and capped with a metering valve. The metering valve releases 80 mg. of composition in an aerosol. The aerosol is inhaled every 4 to 6 hours for prevention of asthmatic attacks.

EXAMPLE 10

After allowing for the differeing solubilities of the compounds and the activity of the particular compound as measured, for example, by the in vivo rat passive cutaneous anaphylaxis assay, a suitable quantity of each of the compounds of Table I through Table IV and Examples 1–2, is substituted for the active compound in the compositions and uses of Examples 3 through 9. Results showing anti-allergy activity are obtained.

It should be noted that in all the compositions and treatment examples of this patent application, the quantity of drug employed refers to the acid equivalent.

It should be noted that there are two systems of nomenclature employed in this application. The nomenclature of FIG. I starts with the number one at the cyano position. However, the numbering of the examples has the one at an oxamate position. Each of the systems is correct and arrives at the same compound. For example, when the oxamate group of FIG. I is at position 4, and $R_1$ and $R_2$ are methyl, the compound of Example 1, dimethyl N,N'-(4-cyano-m-phenylene)dioxamate, is described.

The esters of this case, particularly the dibenzyl and diphenethyl esters, can maintain longer durations of activity in mammals.

When repeated administration is desired, the compounds of this application which have a relatively short duration of activity can be administered in a priming dose-maintenance dose regimen as described in U.S. Ser. No. 316,975 at Page 18, lines 1–21.

We claim:

1. A compound of the formula

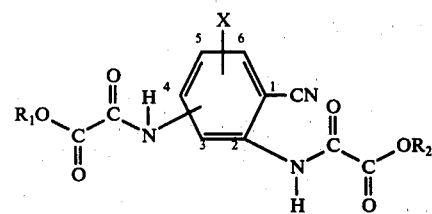

wherein

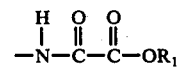

is at one of the positions 4, 5 and 6 with the proviso that where

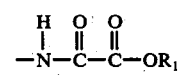

is at 4, then when X is at the 3 position, X is selected from the group consisting of hydrogen and alkyl from one to three carbon atoms, inclusive;

when X is at the 5 position, X is selected from the group consisting of hydrogen, halogen, alkoxy from one to three carbon atoms, inclusive, and cyano; and when X is at the 6 position, X is selected from the group consisting of hydrogen and halogen;

then when X is at the 3 or 6 position, X is hydrogen, and

X is at the 4 position, X is selected from the group consisting of hydrogen, halogen, alkyl from one to three carbon atoms, inclusive; and alkoxy from one to three carbon atoms, inclusive;

when X is at the 3 or 5 position, X is selected from the group consisting of hydrogen and alkyl from one to three carbon atoms, inclusive; and X is at the 4 position, X is selected from the group consisting of hydrogen, alkyl from one to three carbon atoms, inclusive, and cyano;

and $R_1$ and $R_2$ are the same or different and are selected from the group consisting of hydrogen; a physiologically acceptable metal or amine cation; alkyl of one to 12 carbon atoms, inclusive; cycloalkyl of four to eight carbon atoms, inclusive, phenyl and

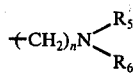

wherein n is an integer of 3 to 4 carbon atoms, inclusive, and $R_5$ and $R_6$ are the same or different and are selected from the group consisting of hydrogen and alkyl of one to four carbon atoms, inclusive, with the proviso that when one of $R_1$ and $R_2$ is hydrogen or a physiologically acceptable metal or amine cation, the other variable is not hydrogen or a physiologically acceptable metal or amine cation.

2. A compound in accordance with claim 1 wherein $R_1$ and $R_2$ are the same or different and are selected from the group consisting of alkyl of one to eight carbon atoms, inclusive.

3. A compound in accordance with claim 2 wherein $R_1$ and $R_2$ are the same or different and are selected from the group consisting of alkyl of four to six carbon atoms, inclusive.

4. A compound in accordance with claim 1 wherein $R_1$ and $R_2$ are the same.

5. A compound in accordance with claim 2 wherein $R_1$ and $R_2$ are the same.

6. A compound in accordance with claim 3 wherein $R_1$ and $R_2$ are the same.

7. A compound in accordance with claim 4 wherein

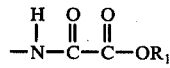

is at the 4 or 5 position and X is hydrogen.

8. A compound in accordance with claim 5 wherein

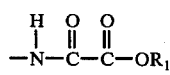

is at the 4 or 5 position and X is hydrogen.

9. A compound in accordance with claim 6 wherein

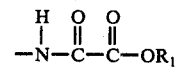

is at the 4 or 5 position and X is hydrogen.

10. A therapeutic composition comprising a compound of the formula

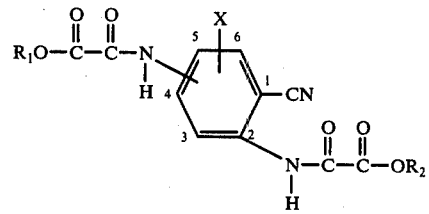

wherein

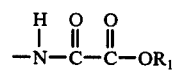

is at one of the positions 4, 5 and 6 with the proviso that where

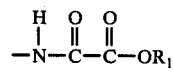

is at 4, then when X is at the 3 position, X is selected from the group consisting of hydrogen and alkyl from one to three carbon atoms, inclusive;

when X is at the 5 position, X is selected from the group consisting of hydrogen, halogen, alkoxy from one to three carbon atoms, inclusive, and cyano; and when X is at the 6 position, X is selected from the group consisting of hydrogen and halogen;

then when X is at the 3 or 6 position, X is hydrogen, and

X is at the 4 position, X is selected from the group consisting of hydrogen, halogen, alkyl from one to three carbon atoms, inclusive; and alkoxy from one to three carbon atoms, inclusive;

when X is at the 3 or 5 position, X is selected from the group consisting of hydrogen and alkyl from one to three carbon atoms, inclusive; an X is at the 4 position, X is selected from the group consisting of hydrogen, alkyl from one to three carbon atoms, inclusive, and cyano;

and $R_1$ and $R_2$ are the same or different and are selected from the group consisting of hydrogen; a physiologically acceptable metal or amine cation; alkyl of one to 12 carbon atoms, inclusive; cycloalkyl of four to eight carbon atoms, inclusive, phenyl and

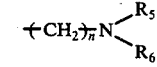

wherein n is an integer of three to four carbon atoms, inclusive, and $R_5$ and $R_6$ are the same or different and are selected from the group consisting of hydrogen and alkyl of one to four carbon atoms, inclusive, with the proviso that when one of $R_1$ and $R_2$ is hydrogen or a physiologically acceptable metal or amine cation, the other variable is not hydrogen or a physiologically acceptable metal or amine cation, in association with a pharmaceutical carrier.

11. A composition in accordance with claim 10 suitable for inhalation administration.

12. A composition in accordance with claim 10 suitable for oral administration.

13. A process for the prophylactic treatment of allergy of a reagin or non-reagin mediated nature in a mammal which comprises administering a compound of the formula

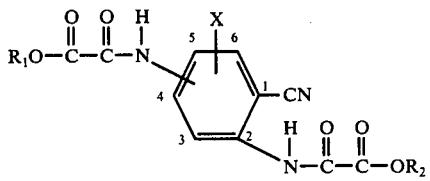

wherein

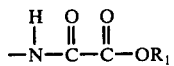

is at one of the positions 4, 5 and 6, with the proviso that where

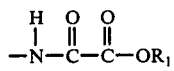

is at 4, then when X is at the 3 position, X is selected from the group consisting of hydrogen and alkyl from one to three carbon atoms, inclusive;
  when X is at the 5 position, X is selected from the group consisting of hydrogen, halogen, alkoxy from one to three carbon atoms, inclusive, and cyano; and
  when X is at the 6 position, X is selected from the group consisting of hydrogen and halogen;
5, then when X is at the 3 or 6 position, X is hydrogen, and
  X is at the 4 position, X is selected from the group consisting of hydrogen, halogen, alkyl from one to three carbon atoms, inclusive; and alkoxy from one to three carbon atoms, inclusive;
6, when X is at the 3 or 5 position, X is selected from the group consisting of hydrogen and alkyl from one to three carbon atoms, inclusive; and
  X is at the 4 position, X is selected from the group consisting of hydrogen, alkyl from one to three carbon atoms, inclusive, and cyano;
and $R_1$ and $R_2$ are the same or different and are selected from the group consisting of hydrogen; a physiologically acceptable metal or amine cation; alkyl of one to 12 carbon atoms, inclusive; cycloalkyl of four to eight carbon atoms, inclusive, phenyl and

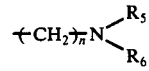

wherein $n$ is an integer of three to four carbon atoms, inclusive, and $R_5$ and $R_6$ are the same or different and are selected from the group consisting of hydrogen and alkyl of one to four carbon atoms, inclusive, with the proviso that when one of $R_1$ and $R_2$ is hydrogen or a physiologically acceptable metal or amine cation, the other variable is not hydrogen or a physiologically acceptable metal or amine cation, in association with a pharmaceutical carrier.

14. A compound in accordance with claim 1 wherein

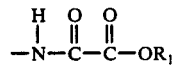

is at the 4 position, X is hydrogen and $R_1$ and $R_2$ are methyl.

15. A compound in accordance with claim 1 wherein

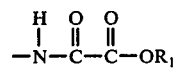

is at the 5 position, X is hydrogen and $R_1$ and $R_2$ are methyl.

* * * * *

UNITED STATES PATENT OFFICE
CERTIFICATE OF CORRECTION

Patent No. 4,067,995          Dated January 10, 1978

Inventor(s) John B. Wright

It is certified that error appears in the above-identified patent and that said Letters Patent are hereby corrected as shown below:

Front Page of Patent:

Line 2, left side: "Wright et al." should read --Wright--.

[75] Inventors:"John B. Wright, Anthony A. Sinkula, both of Kalamazoo, Mich." should read --John B. Wright, Kalamazoo, Michigan--.

Signed and Sealed this

Thirteenth Day of March 1979

[SEAL]

Attest:

RUTH C. MASON
Attesting Officer

DONALD W. BANNER
Commissioner of Patents and Trademarks